(12) United States Patent
Rahman

(10) Patent No.: US 9,999,203 B2
(45) Date of Patent: Jun. 19, 2018

(54) ANIMAL TRAINING USING COGNITIVE ENHANCEMENT

(71) Applicant: Pohela LLC, Santa Monica, CA (US)

(72) Inventor: Muhit Rahman, Santa Monica, CA (US)

(73) Assignee: Pohela LLC, Santa Monica, CA (US)

( * ) Notice: Subject to any disclaimer, the term of this patent is extended or adjusted under 35 U.S.C. 154(b) by 0 days. days.

(21) Appl. No.: 15/462,027

(22) Filed: Mar. 17, 2017

(65) Prior Publication Data

US 2017/0181408 A1    Jun. 29, 2017

Related U.S. Application Data

(62) Division of application No. 14/924,056, filed on Oct. 27, 2015, now Pat. No. 9,616,068.

(60) Provisional application No. 62/069,045, filed on Oct. 27, 2014.

(51) Int. Cl.
| | |
|---|---|
| *A61K 31/16* | (2006.01) |
| *A01K 29/00* | (2006.01) |
| *A61K 31/165* | (2006.01) |
| *A61K 31/13* | (2006.01) |

(52) U.S. Cl.
CPC .............. *A01K 29/00* (2013.01); *A61K 31/13* (2013.01); *A61K 31/165* (2013.01)

(58) Field of Classification Search
USPC .................................................. 514/625, 492
See application file for complete search history.

(56) References Cited

U.S. PATENT DOCUMENTS

| | | | |
|---|---|---|---|
| 4,927,855 A | 5/1990 | Lafon | |
| 5,358,721 A | 10/1994 | Guittard et al. | |
| 5,401,776 A | 3/1995 | Laurent | |
| 5,612,379 A | 3/1997 | Laurent | |
| 5,908,850 A | 6/1999 | Zeitlin et al. | |
| 6,194,000 B1 | 2/2001 | Smith et al. | |
| 6,217,905 B1 | 4/2001 | Edgren et al. | |
| 6,346,548 B1 | 2/2002 | Miller et al. | |
| 6,348,500 B1 | 2/2002 | Fu | |
| 6,489,363 B2 | 12/2002 | Jacobs et al. | |
| 6,992,219 B2 | 1/2006 | Broquaire et al. | |
| 7,057,068 B2 | 6/2006 | Castaldi et al. | |
| 7,087,647 B2 | 8/2006 | Miller et al. | |
| 7,105,486 B2 | 9/2006 | Mickle et al. | |
| 7,115,281 B2 | 10/2006 | Singh et al. | |
| 7,141,555 B2 | 11/2006 | Jacobs et al. | |
| 7,229,644 B2 | 6/2007 | Corvari et al. | |
| 7,235,691 B2 | 6/2007 | Ceausu et al. | |
| 7,297,346 B2 | 11/2007 | Corvari et al. | |
| 7,316,918 B2 | 1/2008 | Riva et al. | |
| 7,317,126 B2 | 1/2008 | Rebiere et al. | |
| 7,368,591 B2 | 5/2008 | Rebiere et al. | |
| 7,405,323 B2 | 7/2008 | Broquaire et al. | |
| 7,541,493 B2 | 6/2009 | Rose | |
| 7,566,805 B2 | 7/2009 | Hickey et al. | |
| 7,576,133 B2 | 8/2009 | Lawyer et al. | |
| 7,649,020 B2 | 1/2010 | Broquaire et al. | |
| 7,704,975 B2 | 4/2010 | Jacobs et al. | |
| 7,779,540 B2 | 8/2010 | McCaffrey et al. | |
| 7,893,289 B2 * | 2/2011 | Goel ..................... | C07C 211/63 546/8 |
| 9,278,094 B2 | 3/2016 | Bear et al. | |
| 2001/0034373 A1 * | 10/2001 | Miller .................. | A61K 31/165 514/625 |
| 2006/0142398 A1 | 6/2006 | Went et al. | |
| 2006/0189694 A1 | 8/2006 | Went et al. | |
| 2006/0252788 A1 | 11/2006 | Went et al. | |
| 2008/0009475 A1 | 1/2008 | Garner et al. | |
| 2008/0227743 A1 | 9/2008 | Nguyen et al. | |
| 2011/0189273 A1 | 8/2011 | Went et al. | |

OTHER PUBLICATIONS

Jacob's CAS: 92: 157783, 1980.
Milgram et al. publication, Neurochem. Research 18(12): 1211-1219, 1993.
Kostarczyk's CAS: 109: 606, 1988.
Mill's publication, Prog Neuropsychopharm. Biol. 25(8), 1597-613, 2001.
Landsberg;s publication, Prog. Neuropsychopharm. Biol. Psychiatry, 29(3): 471-479, 2005.

* cited by examiner

*Primary Examiner* — Rei Tsang Shiao
(74) *Attorney, Agent, or Firm* — Meunier Carlin & Curfman LLC

(57) ABSTRACT

Methods are disclosed to enhance the training potential of a domestic animal during training, thereby shortening the training period and/or increasing the effectiveness of the training. The method involves first administering to the domestic animal a pharmaceutical composition comprising a cognitive enhancing agent in an amount effective to improve cognitive function. The enhanced cognition allows the domestic animal to learn to perform a task and/or to change its existing behavior more effectively and on an accelerated basis. Therefore, while the animal's cognitive function is enhanced, the method then involves conditioning the domestic animal to perform a task or change an existing behavior.

19 Claims, No Drawings

ANIMAL TRAINING USING COGNITIVE ENHANCEMENT

CROSS-REFERENCE TO RELATED APPLICATIONS

This application is a Divisional of U.S. application Ser. No. 14/924,056 filed Oct. 27, 2015, which claims benefit of U.S. Provisional Application No. 62/069,045, filed Oct. 27, 2014, both of which are hereby incorporated herein by reference in their entirety.

BACKGROUND

There are a variety of established methods of animal training, each with its adherents and critics. Some of the better known training procedures include the Koehler method, clicker training, dominance-based training, negative reinforcement, and relationship-based training. The common characteristics of successful methods are knowing the animal's attributes and personality, accurate timing of reinforcement and/or punishment, and consistent communication. However, each of these methods are limited by the inherent learning potential of the animal during conditioning.

SUMMARY

Methods are disclosed to enhance the training potential of a domestic animal during training, thereby shortening the training period and/or increasing the effectiveness of the training. The method involves first administering to the domestic animal, such as a canine subject, a pharmaceutical composition comprising a cognitive enhancing agent in an amount effective to improve cognitive function. While the animal's cognitive function is enhanced, the method then involves conditioning the domestic animal to perform a task or change an existing behavior.

The details of one or more embodiments of the invention are set forth in the accompanying drawings and the description below. Other features, objects, and advantages of the invention will be apparent from the description and drawings, and from the claims.

DETAILED DESCRIPTION

Methods are disclosed to enhance the training potential of a domestic animal, such as a canine subject, during training. By "enhance training" is meant any improvement in the speed, ease, or effectiveness of training. Therefore, the method can shortening the training period, increasing the effectiveness of the training, or a combination thereof.

The method involves first administering to the domestic animal a pharmaceutical composition comprising a cognitive enhancing agent in an amount effective to improve cognitive function. The enhanced cognition allows the domestic animal to learn to perform a task and/or to change its existing behavior more effectively and on an accelerated basis. Therefore, while the animal's cognitive function is enhanced, the method then involves conditioning the domestic animal to perform a task or change an existing behavior.

Cognitive Enhancing Agent

In some embodiments, the cognitive enhancing agent is any molecule, compound, or composition that is known or purported to enhance cognitive function in mammals. In some embodiments, the cognitive enhancing agent comprises a psychostimulant (CNS stimulant) drug. For example, the psychostimulant drug can be a phenethylamine derivative, which has the general chemical formula:

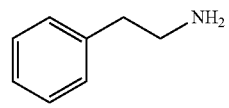

Phenethylamine derivatives include substituted phenethylamines, substituted amphetamines, and substituted methylenedioxyphenethylamines. Non-limiting examples of phenethylamine derivatives include amphetamine, methylphenidate, dexmethylphenidate, dextroamphetamine, mixed amphetamine salts, dextromethamphetamine, lisdexamfetamine, p-methoxyamphetamine, methylenedioxyamphetamine, 2,5-dimethoxy-4-methylamphetamine, 2,4,5-trimethoxyamphetamine, and 3,4-methylenedioxymethamphetamine, N-ethylamphetamine, fenethylline, benzphetamine, and chlorphentermine. The amphetamine can have any stereogenic configuration, including both dextro- and levo-isomers. In some cases, the psychostimulant drug contains combinations of active ingredients and/or mixtures of stereoisomer salts. For example, Adderall® (amphetamine, dextroamphetamine mixed salts) is a mixture of amphetamine stereoisomer salts and inactive ingredients. The active ingredients of Adderall® by salt content are 75% dextroamphetamine salts and 25% levoamphetamine salts.

In some cases, the substituted phenethylamine comprises methylphenidate (trade names: CONCERTA, METHYLIN, RITALIN, EQUASYM XL), which has the general chemical formula:

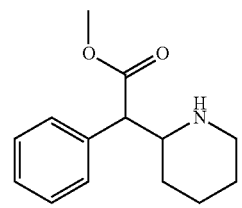 [SMILES: COC(=O)C(c1ccccc1)C1CCCCN1]

Amino acid methylphenidate prodrugs may be prepared via the general methods described in U.S. Pat. No. 7,105,486 (which is incorporated herein in its entirety by reference for the preparation of amphetamine amino acid prodrugs). Amino acid methylphenidate prodrugs may comprise methylphenidate covalently bound to a single amino acid at the piperidine nitrogen or bound to a di- or tri-peptide at this position. It is also a matter of routine organic synthesis to prepare carboxamide and carbamate methylphenidate prodrugs by reacting methylphenidate with an aliphatic aldehyde or aliphatic organic acid. Methylphenidate contains a secondary amine group and amphetamine contains an amino group both of which may be reacted to form prodrugs having a chemical moiety covalently attached to the amine or amino group of the parent drug compound. Methylphenidate possesses two centers of chirality and thus can exist as four separate optical isomers. For example, the 2R:2'R isomer of methylphenidate is disclosed in U.S. Pat. No. 5,908,850 which is incorporated herein in its entirety by reference.

In some cases, the phenethylamine derivatives comprises amphetamine, which has the chemical formula:

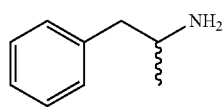

Amphetamine prodrugs, and methods of preparing amphetamine prodrugs, have been described previously, U.S. Pat. No. 7,105,486, which describes the preparation of lisdexamfetamine, is hereby incorporated by reference at cols. 20 to 22 for its teachings regarding the synthesis of amino acid amphetamine prodrugs. In addition to amino acid prodrugs it is possible to prepare a number of other amphetamine prodrugs by reacting the amphetamine amino group with a chemically labile moiety. It is within the ability of those of ordinary skill in the art of chemical synthesis to prepare carboxamide amphetamine prodrugs by reacting amphetamine with an aliphatic aldehyde and to prepare carbamate amphetamine prodrugs by reacting amphetamine with an aliphatic organic acid. The term "lisdexamfetamine" also encompasses any pharmaceutically acceptable salt, polymorph or ester thereof. Lisdexamfetamine is typically administered as a dimesylate salt but includes all pharmaceutically acceptable salts of lisdexamfetamine free base. Lisdexamfetamine dimesylate (CAS Reg. No. 608137-32-3, (2S)-2,6-diamino-N-[(1S)-1-methyl-2-phenylethyl]hexanamide dimethanesulfonate) is an amphetamine prodrug in which L-lysine is covalently bound to d-amphetamine.

In some cases, the psychostimulant drug comprises modafinil, which has the chemical formula:

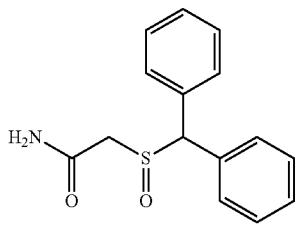 [SMILES: NC(=O)CS(=O)C(c1ccccc1)c1ccccc1]

Modafinil can be synthesized by the method as described in U.S. Pat. No. 4,927,855, which is incorporated herein by reference. In some embodiments, the psychostimulant drug comprises an acetamide derivative modafinil, such as 2-(benzhydrylsulfinyl)acetamide. In some embodiments, modafinil polymeric forms can be used, such as those disclosed in U.S. Pat. Nos. 7,649,020; 7,405,323; 6992,219, as well as enantiomers, analogues and derivatives can be used which are disclosed in U.S. Pat. Nos. 7,704,975; 7,779,540; 7,576,133; 7,566,805; 7,541,493; 7,368,591; 7,317,126; 7,316,918; 7,297,346; 7,235,691; 7,229,644; 7,141,555; 7,115,281; 7,087,647; 7,057,068; 6,489,363; 6,348,500; 6,346,548; 5,612,379; 5,401,776, each of which are incorporated herein in their entirety by reference.

In some cases, the psychostimulant drug comprises amantadine (trade name: SYMMETREL), which has the following chemical formula:

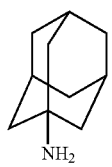

Extended release forms of amantadine have been described in the art. U.S. Pat. No. 5,358,721, to Guittard et al., and U.S. Pat. No. 6,217,905, to Edgren et al., which are incorporated herein in their entirety by reference. U.S. Pat. No. 6,194,000, to Smith et al., incorporated herein in their entirety by reference, discloses analgesic immediate and controlled release pharmaceutical compositions utilizing NMDA receptor antagonists, such as amantadine, as the active agent. U.S. Patent Appl. Publication Nos. US 2006/0252788, US 2006/0189694, US 2006/0142398, and US 2008/0227743, incorporated herein in their entirety by reference, all to Went et al., each disclose the administration of an NMDA receptor antagonist, such as amantadine, optionally in controlled release form. U.S. Patent application US 2011/0189273 also incorporated herein in its entirety by reference, discloses alternative formulations of amantidine.

In some embodiments, the psychostimulant drug comprises a γ-aminobutyric acid (GABA) antagonists. Examples of GABA antagonists include Bicuculline and Metrazol (pentylenetetrazol), and the benzodiazepine GABA receptor antagonist Flumazenil. Thujone and muira puama may have properties of GABA receptor antagonism.

Pentylenetetrazol has the following chemical formula:

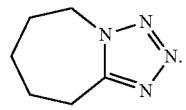

Several classes of compounds can modulate the pentylenetetrazol discriminative stimulus including 5-HT1A, 5-HT3, NMDA, glycine, and L-type calcium channel ligands.

Bicuculline is a light-sensitive competitive antagonist of GABAA receptors. Bicuculline has the following chemical formula:

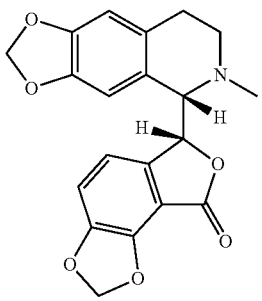 [SMILES: CN1CCc2cc3c(cc2[C@H]1[C@@H]1OC(=O)c2c1ccc1c2OCO1)OCO3]

The action of bicuculline is primarily on the ionotropic GABAA receptors, which are ligand-gated ion channels concerned chiefly with the passing of chloride ions across the cell membrane, thus promoting an inhibitory influence on the target neuron. These receptors are the major targets for benzodiazepines and related anxiolytic drugs.

In some embodiments, the psychostimulant drug comprises a selective serotonin reuptake inhibitor (SSRI). Non-limiting examples of SSRIs include citalopram, dapoxetine, escitalopram, fluoxetine, fluvoxamine, indalpine, paroxetine, sertraline, and zimelidine.

Citalopram (trade names: CELEXA, CIPRAMIL) has one stereocenter, to which a 4-fluorophenyl group and an N,N-dimethyl-3-aminopropyl group bind. As a result of this chirality, the molecule exists in (two) enantiomeric forms (mirror images). They are termed S-(+)-citalopram and R-(−)-citalopram. Citalopram therefore has the following chemical formulas:

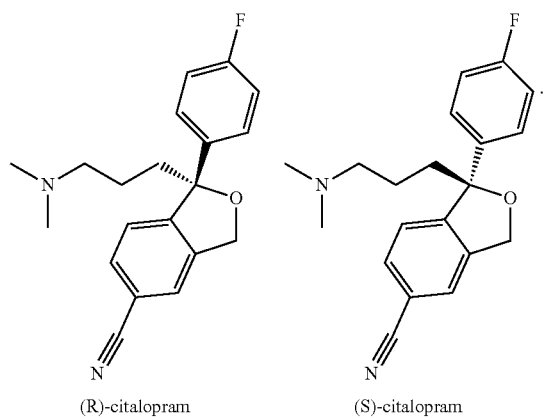

(R)-citalopram    (S)-citalopram

Fluvoxamine (trade names: FLOXYFRAL, LUVOX, FEVARIN) has the following chemical formula:

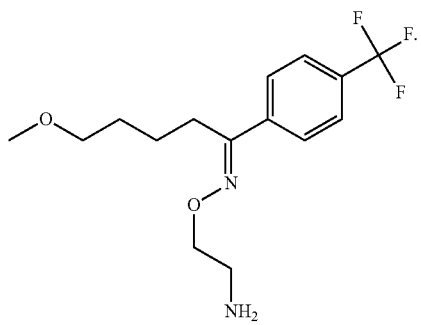 [SMILES: COCCCC/C(=N\OCCN)c1ccc(C(F)(F)F)cc1]

Escitalopram (trade names: LEXAPRO CIPRALEX) has the following chemical formula:

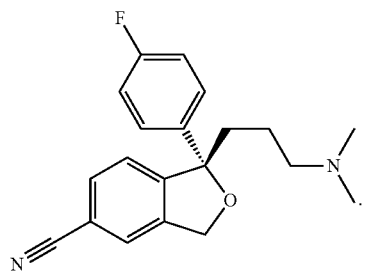 [SMILES: CN(C)CCC[C@@]1(c2ccc(F)cc2)OCc2cc(C#N)ccc21]

Paroxetine (trade name: PAXIL) has the following chemical formula:

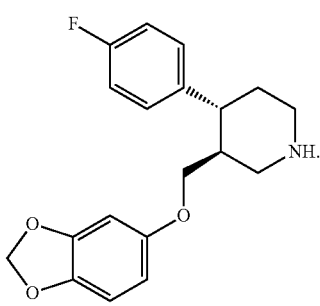 [SMILES: Fc1ccc([C@@H]2CCNC[C@H]2COc2ccc3c(c2)OCO3)cc1]

Sertraline (trade names: ZOLOFT, LUSTRAL) has the following chemical formula:

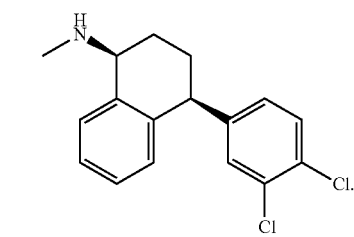 [SMILES: CN[C@H]1CC[C@@H](c2ccc(Cl)c(Cl)c2)c2ccccc21]

Fluoxetine (trade names: PROZAC, SARAFEM, LADOSE, FONTEX) has the following chemical formula:

In some embodiments, the cognitive enhancing agent is a natural product or dietary supplement that enhances cognition, such an herb or plant extract. However, in some embodiments, the disclosed methods include at least one cognitive enhancing agent that is not a natural product or dietary supplement.

For example, green tea and other natural and synthetic sources of catechins, and bioflavanoids, flavanols, flavandiols, flavanoids, and tannins or derivatives thereof, can enhance cognitive ability.

Caffeine, when consumed in conjunction with L-theanine, a common amino acid found in green tea, creates more long-lasting and beneficial effects, including a boost to working memory, rapid visual information processing, and especially attention switching (i.e. reduced distractibility). The reason this works is that the L-theanine, which can cross the blood-brain barrier, counteracts the negative stimulant effects of caffeine, including anxiety and increased blood pressure.

Creatine has also been shown to improve memory and attention span. It plays a pivotal role in brain energy homeostasis, acting as a buffer for cytosolic and mitochondrial pools of cellular energy.

Piracetam, also known as Nootropyl or Lucetam, works by improving the functioning of (ACh) transmitters and receptors. This can be ingested with choline to experience its benefits, including increased mental clarity, spatial memory, and an overall boost in brain functioning.

Found primarily in northern India, *Bacopa monnieri* is a perennial creeping herb that's been used for centuries to enhance memory, learning, and overall cognitive performance (in addition to its use as an anti-inflammatory, analgesic, antipyretic, and sedative). The active ingredients responsible for these effects include sulfhydryl and polyphenol, compounds that lessen oxidative stress.

*Ginkgo Biloba* extract comes from maidenhair, an extremely unique tree native to China that has no relatives—what is considered a living fossil. Extracts of *Ginkgo* leaves contain flavonoid glycosides and terpenoids (ginkgolides, bilobalides) which are renowned for their pharmacological benefits, including their ability to improve memory and concentration.

Asian ginseng can be used to improve working memory, attention, calmness, mood, and even reduce fatigue.

*Rhodiola rosea* has an affect on serotonin and dopamine levels due to monoamine oxidase inhibition. *Rhodiola rosea* can improve cerebral functions (such as associative thinking, short-term memory, calculation, ability of concentration, and speed of audio-visual perception).

Found in Spain and southern France, *Salvia lavandulaefolia* is an aromatic herb that boosts acetylcholine function. Studies have shown that it can enhance memory.

Veterinary Pharmaceutical Formulation

Disclosed are veterinary pharmaceutical formulations containing therapeutically effective amounts of one or more of the disclosed cognitive enhancing agents and a pharmaceutically acceptable carrier. Pharmaceutical carriers suitable for veterinary administration of the compounds provided herein include any such carriers known to those skilled in the art to be suitable for the particular mode of administration. For example, physiologically acceptable formulation excipients are described in "Gennaro, Remington: The Science and Practice of Pharmacy" (20th Edition, 2000), which is incorporated by reference herein. All ingredients, carriers and excipients may be substantially pharmaceutically or veterinary pure and non-toxic in the amounts employed and may be compatible with the pharmaceutically active ingredients.

The formulations can be administered directly or in the form of suitable preparations, enterally, parenterally or dermally. Enteral administration of the formulations takes place, for example, orally in the form of powder, tablets, capsules, pastes, potions, granules, orally administered solutions, suspensions and emulsions, boli, medicated feed or drinking water.

Suitable preparations include oral solutions and concentrates for oral administration after dilution; emulsions and suspension for oral administration; and semisolid preparations; formulations in which the active compound is processed in an ointment base or in an oil-in-water or water-in-oil emulsion base; solid preparations, such as powders, premixes or concentrates, granules, pellets, tablets, caplets, boli and capsules, with tablets the preferred form; and oral solutions prepared by dissolving the active compound in a suitable solvent and, if appropriate, adding additives such as solubilizers, acids, bases, buffer salts, antioxidants and preservatives. Suitable solvents may include physiologically acceptable solvents, such as water, alcohols, such as ethanol, butanol, benzyl alcohol, glycerol, propylene glycol and polyethylene glycol, N-methylpyrrolidone, and mixtures of the same. The active compounds can, if appropriate, also be dissolved in physiologically acceptable vegetable or synthetic oils. Solubilizers may include solvents which promote dissolution of the active compound in the main solvent or substances which prevent precipitation of the active compound. Examples are polyvinyl pyrrolidone, polyoxyethylated castor oil and polyoxyethylated sorbitan esters.

By mixing an active ingredient with a carrier in the liquid phase, the active can become "encapsulated" or substantially covered in a matrix of carrier after the spray granulation process. Granulation is generally performed by spraying liquid into the fluidized powder. The granules can subsequently be dried with heated air.

Suitable excipients may include physiologically acceptable inert solids such as, for example, sodium chloride, calcium carbonate, hydrogen carbonates, aluminum oxides, silicas, clays, precipitated or colloidal silicon dioxide and phosphates. Additional excipients that can be present in the formulation include fillers, antioxidants, colorants, flavors, sugar components, surfactants, stabilizers, flow agents, disintegration agents, preservatives, and/or lubricating agents.

Additional suitable auxiliaries can include lubricants, such as, for example, magnesium stearate, stearic acid, talcum and bentonites, disintegration-promoting substances, such as starch or transversely crosslinked polyvinyl pyrrolidone, binders, such as, for example, starch, gelatin or linear polyvinyl pyrrolidone, and dry binders, such as microcrystalline cellulose. Other suitable excipients include sugar, cellulose, carboxymethyl cellulose, Aerosil, nutrients and feedstuffs, such as milk powder and pork liver powder, animal meals, ground and crushed cereal meals, Avicel PH102, and starches.

In some embodiments, the solid oral dosage form is a soft chew. In soft chew formulations the forming agent is important for the texture of the soft chew and the possibility to form single soft chews from the dough that stay intact and separate. Forming agents are agents providing texture to the soft chew product, like for example polyethylene glycol (PEG), microcrystalline wax, cetyl alcohol or polyvinylpyrrolidone (PVP). In an embodiment, the forming agent is polyethylene glycol (PEG). Moreover, depending upon the desired consistency of the soft chew, different molecular weight PEG may be utilized. In an embodiment, PEG 8000 is utilized. However, the PEG chosen is a matter of choice and the molecular weight may be higher or lower than 8000, but preferably higher than 600. Alternatively PEG 3500 might be used.

The materials in the final formulation, such as the excipients, auxiliaries, synergists and other materials, which aid in delivery, shelf-life, desired physical structure and so forth will be referred to herein generally as carrier material. As stated herein, carrier material could be pharmaceutically active under certain circumstances.

The disclosed pharmaceutical composition can be administered in an amount effective to enhance the canine subject's cognitive ability during the training period. Therefore, the effective dosage can be empirically determined based on the specific drug and route of administration.

In one embodiment, cognitive enhancing agent is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight; and from about 100 µg to about 500 µg to per kg of body weight. Alternatively, the amount of cognitive enhancing agent administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In some embodiments, the pharmaceutical composition is administered at least 1, 2, 3, 4, 5, 6, 7, 8, 9, 10, 11, 12, 13, 14, 15, 16, 17, 18, 19, 20, 21, 22, 23, or 24 hours prior to a conditioning activity. The training period can last from 1 day to several weeks or more. Therefore, the pharmaceutical composition can be administered every 1, 2, 3, 4, 5, 6, 7, days or more, during the training period. In some cases, administration of the pharmaceutical composition is continued at least 1, 2, 3, 4, 5, 6, 7, or more days after training has completed.

Domestic Animals

The disclosed methods may in some embodiments be used to enhance the training of any domestic mammal. Non-limiting examples of domestic mammals include dogs (*Canis lupus familiaris*), cat (*Fells silvestris catus*), ferret (*Mustela putorius furo*), sheep (*Ovaris aries*), pig (*Sus scrofa domesticus*), goat (*Capra aegagrus hircus*), horse (*Equus ferus caballus*), or cattle (*Bos primigenius Taurus*). The animal can be a companion animal, such as a dog, cat, or ferret. The animal can also be a circus animal, such as an elephant, lion, tiger, or non-human primate, or a marine mammal, such as a seal, whale, dolphin, otter, or walruses.

In particular embodiments, the disclosed methods is used to enhance training of a canine animal of the species *Canis lupus familiaris* (a.k.a, domestic dog). For example, the American Kennel Club (AKC) recognizes 152 breeds of dog distributed in seven breed groups (Herding, Hound, Nonsporting, Sporting, Terrier, Toy, and Working). Non-limiting examples of dog breeds whose training can be enhanced with the disclosed methods include, but are not limited to, Afghan Hound, Airedale Terrier, Akita, Alaskan Malamute, American Eskimo Dog, American Foxhound, American Hairless Rat Terrier, American Staffordshire Terrier, American Water Spaniel, Australian Cattle Dog, Australian Shepherd, Australian Terrier, Basenji, Basset Hound, Beagle, Bearded Collie, Bedlington Terrier, Belgian Laekenois, Belgian Malinois, Belgian Sheepdog, Belgian Tervuren, Bernese Mountain Dog, Bichon Frise, Bloodhound, Border Collie, Border Terrier, Borzoi, Boston Terrier, Bouvier des Flandres, Boykin Spaniel, Boxer, Briard, Brittany, Bulldog, Brussels Griffon, Bullmastiff, Bull Terrier, Cairn Terrier, Cardigan Welsh Corgi, Cavalier King Charles Spaniel, Chesapeake Bay Retriever, Chihuahua, Chinese Crested, Chinese Shar-Pei, Chow Chow, Clumber Spaniel, Cocker Spaniel, Collie, Curly-Coated Retriever, Dachshund, Dalmatian, Dandie Dinmont Terrier, Doberman Pinscher, Dogo Canario, English Cocker Spaniel, English Foxhound, English Setter, English Springer Spaniel, Entlebucher Mountain Dog, Field Spaniel, Flat-Coated Retriever, French Bulldog, German Longhaired Pointer, German Shepherd Dog, German Shorthaired Pointer, German Wirehaired Pointer, Giant Schnauzer, Golden Retriever, Gordon Setter, Great Dane, Great Pyrenees, Greater Swiss Mountain Dog, Greyhound, Harrier, Havanese, Ibizan Hound, Irish Setter, Irish Terrier, Irish Water Spaniel, Irish Wolfhound, Italian Greyhound, Jack Russell Terrier, Keeshond, Kerry Blue Terrier, Komondor, Kuvasz, Labrador Retriever, Leonberger, Lhasa Apso, Lowchen, Maltese, Manchester Terrier—Standard, Manchester Terrier—Toy, Mastiff, Miniature Bull Terrier, Miniature Pinscher, Miniature Poodle, Miniature Schnauzer, Munsterlander, Neapolitan Mastiff, Newfoundland, New Guinea Singing Dog, Norwegian Elkhound, Norwich Terrier, Old English Sheepdog, Papillon, Pekingese, Pembroke Welsh Corgi, Petit Basset Griffon Vendeen, Pharaoh Hound, Pointer, Polish Lowland Sheepdog, Pomeranian, Portuguese Water Dog, Presa Canario, Pug, Puli, Pumi, Rhodesian Ridgeback, Rottweiler, Saint Bernard, Saluki, Samoyed, Schipperke, Scottish Deerhound, Scottish Terrier, Silky Terrier, Shetland Sheepdog, Shiba Inu, Shih Tzu, Siberian Husky, Smooth Fox Terrier, Soft Coated Wheaten Terrier, Spinone Italiano, Staffordshire Bull Terrier, Standard Poodle, Standard Schnauzer, Sussex Spaniel, Tibetan Spaniel, Tibetan Terrier, Toy Fox Terrier, Toy Poodle, Vizsla, Weimaraner, Welsh Springer Spaniel, Welsh Terrier, West Highland White Terrier, Wirehaired Pointing Griffon, Whippet, Yorkshire Terrier.

The methods can be used for animals of any age or health. For example, in some cases, the animal is a juvenile dog, an adolescent dog, an adult dog, or a senior dog. Therefore, the animal can be a canine subject from two to six months in age, from six to eighteen months in age, from twelve months to three years in age, or from six to ten years in age.

In some embodiments, the animal is a healthy animal, such as an animal that has not been diagnosed with a cognitive deficit or any other neurological disease.

Canine Conditioning

The disclosed methods can be used with any forms of conditioning suitable to train domestic animals. For example, conditioning can involve training the animal for a task selected from the group consisting of agility, hunting, herding, tracking, detection, assistance, search and rescue, and guarding. The disclosed method can also be used to train domestic animals to refrain from unwanted behavior. For example, the method can involve housebreaking the domestic animal. Animal training can involve socialization of the domestic environment, basic obedience training, or training for specialized activities including law enforcement, search and rescue, hunting, working with livestock, assistance to people with disabilities, entertainment, dog sports, detection and protecting people or property.

The disclosed methods can be used with obedience training, to train service animals (e.g., Seeing Eye dogs, health assistance dogs, and companion dogs), to train military and police dogs (e.g., to detect drugs and/or explosives, apprehend subjects, and guard people or locations), or to train animals to perform tricks.

There are a variety of established methods of animals training that can be used with the disclosed methods, each with its adherents and critics. Some of the better known training procedures include the Koehler method, clicker training, dominance-based training, negative reinforcement and relationship-based training. The common characteristics of successful methods are knowing the animal's attributes and personality, accurate timing of reinforcement and/or punishment and consistent communication.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for enhancing training of a canine subject, comprising
    (a) administering to the canine subject a pharmaceutical composition comprising a cognitive enhancing agent in an amount effective to improve cognitive function, wherein said cognitive enhancing agent is an acetamide derivative of modafinil; and
    (b) conditioning the canine subject to perform a task or change an existing behavior.

2. The method of claim 1, wherein the conditioning comprises housebreaking the canine subject.

3. The method of claim 1, wherein the conditioning comprises training the subject for a task selected from the group consisting of agility, hunting, herding, tracking, detection, assistance, search and rescue, and guarding.

4. The method of claim 1, wherein the canine subject is a juvenile dog.

5. The method of claim 1, wherein the canine subject is an adolescent dog.

6. The method of claim 1, wherein the canine subject is an adult dog.

7. The method of claim 1, wherein the canine subject is a senior dog.

8. The method of claim 1, wherein the canine subject is from two to six months in age.

9. The method of claim 1, wherein the canine subject is from six to eighteen months in age.

10. The method of claim 1, wherein the canine subject is from twelve months to three years in age.

11. The method of claim 1, wherein the canine subject is from six to ten years in age.

12. The method of claim 1, wherein the pharmaceutical composition is administered at least daily over a period of 1 to 90 days.

13. The method of claim 1, wherein the pharmaceutical composition is administered as a controlled release formulation that provides an effective dose over a period of 1 to 90 days.

14. The method of claim 1, wherein the pharmaceutical composition is administered at least one hour before conditioning.

15. The method of claim 14, wherein the pharmaceutical composition is administered from 1 to 24 hours before conditioning.

16. The method of claim 1, wherein the pharmaceutical composition is administered during conditioning and for at least one day after conditioning.

17. The method of claim 1, wherein the canine subject has not been diagnosed with a cognitive deficit.

18. The method of claim 1, wherein the modafinil acetamide derivative is 2-(benzhydrylsulfinyl)acetamide.

19. The method of claim 1, wherein the modafinil is in polymeric form.

* * * * *